United States Patent [19]

Casara et al.

[11] Patent Number: 5,817,647
[45] Date of Patent: Oct. 6, 1998

[54] UNSATURATED ACETYLENE PHOSPHONATE DERIVATIVES OF PURINES

[75] Inventors: Patrick Casara, Ittenheim; Jean-François Navé, Strasbourg; Serge Halazy, Lagarrigue, all of France

[73] Assignee: Merrell Pharmaceuticals Inc., Cincinnati, Ohio

[21] Appl. No.: 505,168

[22] PCT Filed: Feb. 25, 1994

[86] PCT No.: PCT/US94/01837

§ 371 Date: Nov. 17, 1995

§ 102(e) Date: Nov. 17, 1995

[87] PCT Pub. No.: WO94/22882

PCT Pub. Date: Oct. 13, 1994

[30] Foreign Application Priority Data

Apr. 1, 1993 [EP] European Pat. Off. ............ 93400842

[51] Int. Cl.$^6$ ................ A61K 31/675; C07F 9/6512
[52] U.S. Cl. ................... 514/81; 544/244; 544/265; 558/187; 558/189; 514/262
[58] Field of Search ................. 544/243, 244, 544/265; 514/81, 262

[56] References Cited

U.S. PATENT DOCUMENTS

| 5,032,592 | 7/1991 | Hughes et al. | 514/256 |
|---|---|---|---|
| 5,055,458 | 10/1991 | Bailey et al. | 544/244 |
| 5,166,198 | 11/1992 | Harnden et al. | 514/81 |
| 5,532,225 | 7/1996 | Reist et al. | 514/81 |

FOREIGN PATENT DOCUMENTS

| 0173624 | 3/1986 | European Pat. Off. . |
|---|---|---|
| 0253412 | 1/1988 | European Pat. Off. . |
| 0353955 | 2/1990 | European Pat. Off. . |
| 0481214 | 4/1992 | European Pat. Off. . |
| 0532423 | 3/1993 | European Pat. Off. . |
| 9201698 | 2/1992 | WIPO . |
| 9209611 | 6/1992 | WIPO . |
| 9307157 | 4/1993 | WIPO . |

OTHER PUBLICATIONS

J. Org. Chem (1992) vol. 57, No. 8, pp. 2320–2327—Sreenivasulu Megati et al. "Unsaturated phosphonates as acyclic nucleotide analogues. Anomalous Michaelis–Arbuzov and Michaelis–Becker reactions with multiple bond".

J. Med. Chem. (1993) vol. 36, No. 10, pp. 1343–1355—M.R. Harden et al. "Novel acyclonucleotides: synthesis and antiviral activity of alkenylphosphonic acid derivatives of purines and a pyrimidine".

Primary Examiner—Mukund J. Shah
Assistant Examiner—Pavanaram K. Sripada
Attorney, Agent, or Firm—Mark C. Nelligan

[57] ABSTRACT

Disclosed are novel unsaturated acetylene phosphonate derivatives of certain purines or pyrimidines useful as antiviral agents, methods useful for their preparation and use of these compounds as antiviral agents effective against DNA viruses, retroviruses and viruses involved in tumor formation.

9 Claims, No Drawings

UNSATURATED ACETYLENE PHOSPHONATE DERIVATIVES OF PURINES

This application is a 371 of PCT/US94/01837 Feb. 25, 1994.

The present invention comprises unsaturated phosphonate derivatives of certain purines or pyrimidines useful as anti-viral agents, to methods and intermediates useful for their preparation and to their end-use application as antiviral agents effective against DNA viruses (herpes viruses 1 and 2, cytomegalovirus, varicella-zoster virus, Epstein-Barr virus), retroviruses (human immunodeficiency viruses 1 and 2 and visna virus) and against viruses involved in tumor formation.

BACKGROUND OF THE INVENTION

Certain derivatives of purine or pyrimidine bases have shown antiviral and antitumor activity. For example, see EP 0 173,624; EP 0 253,412; EP 0 353,955; WO 92/01698; EP 0 481,214; and *J. Org. Chem.* 57: 2320–2327 (1992). The compounds of the present invention represent novel compounds derived from purine and pyrimidine bases.

SUMMARY OF THE PRESENT INVENTION

More specifically this invention relates to novel compounds of Formula I and Formula II:

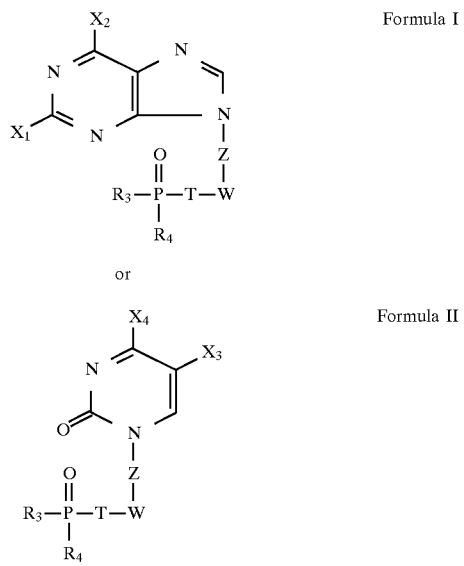

the stereoisomeric forms, tautomeric forms and the pharmaceutically acceptable salts thereof, wherein $X_1$ is H or $NH_2$;
$X_2$ is OH or $NH_2$;
$X_3$ is H or $CH_3$; and
$X_4$ is $NH_2$ or OH;
Z is nothing, $CH_2$, $CH_2CH_2$, $CH_2O$, or $CH_2OCH_2$;

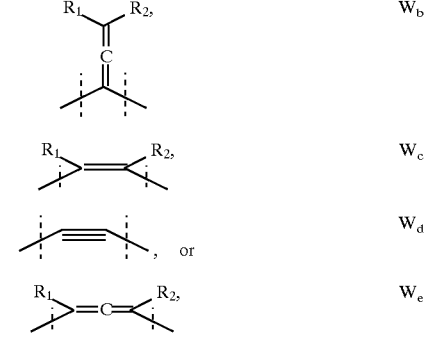

wherein each of $R_1$ and $R_2$ are independently H, F or $CH_2OH$;

T is nothing, T' or T", wherein
T' is $CH_2CH_2$, $CH=CH$, $CH_2CH(OH)$, $CH_2CH(CH_2OH)$, or $CH_2CH(CH_2F)$, and
T" is $CH=CH-CH(OH)$, $CH=CH-CH(CH_2OH)$, $CH_2OCH_2$, $CH_2OCH(CH_2OH)$, $CH_2CH(CH_2OH)CH_2$, $CH_2CH_2CH(OH)$, $CH_2CH_2CH(CH_2OH)$, or $CH_2CH_2CH(CH_2F)$; and $R_3$ and $R_4$ are each independently OH, $OR_5$, $OR_5'$ or $-O-CH(R_6)-O-C(O)R_5$, provided that when one of $R_3$ or $R_4$ is OH then the other is not $-O-CH(R_6)-O-C(O)R_5$, wherein $R_5$ and $R_5'$ are each independently $C_{1-15}$ alkyl or benzyl, and $R_6$ is H or $C_{1-10}$ alkyl, provided that when T is $CH=CH$ or $CH_2CH_2$, W is $W_c$, and Z is $CH_2$, then $X_1$ is not $NH_2$ and $X_2$ is not OH simultaneously;

provided that when W is $W_e$, then Z is nothing or $CH_2$.

provided that when T is nothing then W is not $W_c$, provided that when Z is $CH_2$ and W is Wa, then T cannot be $CH=CH$, and provided that when Z is nothing and $W=W_c$, then T is not $CH=CH$.

The present invention also comprises using the compounds of Formula I and Formula II to prepare a pharmaceutical composition for treating viral infections.

DETAILED DESCRIPTION OF THE PRESENT INVENTION

The compounds of the present invention are purine derivatives (Formula I) or pyrimidine derivatives (Formula II), herein referred to as nucleic bases (dotted line representing the attachment to the rest of the molecule):

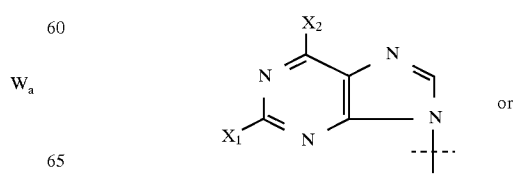

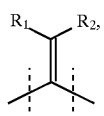

-continued

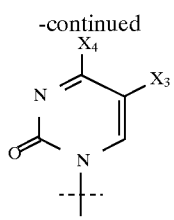

having a phosphonate moiety. Linking the phosphonate moiety to the purine or pyrimidine derivative are moieties T, W and Z groups. An example of the attachment of these moieties to the rest of the molecule follows where T is T" and is CH=CH—CH(CH$_2$OH), W is W$_a$ wherein R$_1$ and R$_2$ are each H, and Z is CH$_2$O:

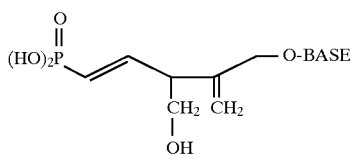

The following combinations, being smaller molecules of the present invention, are preferred.

when W=W$_a$ or W$_b$ and T=T" then Z is not CH$_2$OCH$_2$;
when W=W$_c$ or W$_d$ and T=T' then Z is not CH$_2$OCH$_2$;
when W=W$_c$ or W$_d$ and T=T''' then Z is CH$_2$.

Other preferred compounds are when T is T', and more preferably T' is CH=CH; when T is T'', and more preferably T''' is CH$_2$OCH$_2$; when W is W$_a$, W$_c$ or W$_d$; when each of R$_1$ and R$_2$ is H; and/or Z is CH$_2$, CH$_2$CH$_2$ or CH$_2$O. Formula I is preferred over Formula II. Preferred pyrimidine type bases are cytosine, uracil, and thymine. Preferred purine bases are 2,6-diaminopurine (DAP), guanine and adenine.

As used herein the proviso "when T is CH=CH or CH$_2$CH$_2$, W is W$_c$ and Z is CH$_2$ then X$_1$ is not NH$_2$ and X$_2$ is not OH simultaneously" is meant to exclude compounds from the claims where guanine (X$_1$=NH$_2$ and X$_2$=OH simultaneously) is the base. This proviso excludes two compounds where guanine is the base: when (1) T is CH=CH, W is W$_c$ and Z is CH$_2$, and (2) T is CH$_2$CH$_2$, W is W$_c$ and Z is CH$_2$.

The term C$_{1-10}$ alkyl or C$_{1-15}$ alkyl means respectively an alkyl moiety having between 1 to 10 carbon atoms or 1 to 15 carbon atoms. The alkyl moiety may be straight-chain or branched, e.g., tert-butyl. For the C$_{1-15}$ alkyl moiety, C$_{1-10}$ alkyl is preferred and C$_{1-6}$ more preferred and C$_{1-3}$ most preferred. For the C$_{1-10}$ alkyl moiety, C$_{1-6}$ is preferred and C$_{1-3}$ most preferred.

The term "pharmaceutically acceptable salts" means both acid addition salts and metal and amine salts which are known to be non-toxic and useful derivatives in the preparation of pharmaceutical formulations suitable for end-use applications.

Pharmaceutically acceptable acid addition salts include the known non-toxic organic or inorganic acid addition salts of the base compounds of Formula I and Formula II. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in an aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic forms, demonstrate higher melting points and an increased stability.

Pharmaceutically acceptable metal and amine salts are those salts which are stable under ambient conditions, and wherein the cation does not contribute significantly to the biological activity of the salt. Suitable metal salts include the sodium, potassium, calcium, barium, zinc, and aluminium salts. The sodium and potassium salts are preferred. Suitable amine salts are prepared from amines which have sufficient basicity to form a stable salt, and preferably include those amines which are frequently used in medicinal chemistry because of their low toxicity and acceptability for medical use. These include the trialkylamines such as triethylamine, and others including procaine, dibenzylamine, N-benzyl-betaphenethylamine, ephenamine, and N,N'-dibenzylethylenediamine, dehydroabietylamine, N-ethylpiperidine, benzylamine, and dicyclohexylamine.

"Stereoisomeric forms" of the compounds of Formula I and Formula II is a general term for all isomers of these compounds that differ only in the orientation of their atoms in space which include mirror image isomers (enantiomers), geometric (cis/trans) isomers, and isomers of drugs with more than one chiral center that are not mirror images of one another (diastereoisomers). Mixtures may be resolved or isolated according to conventional and standard procedures well known in the art, e.g., chromatographic separation, fractional crystallization, use of optically active acids, enzymatic resolution and the like. Tautomeric enol-keto forms may exist at the 6-position of the purine nucleus, and the pyrimidine will exhibit amineimine tautomeric forms. Although the moiety "W$_c$" may be drawn as cis herein, it is understood that both forms cis-and trans- are meant to be depicted.

The compounds of this invention may be prepared by the application of analogous chemical reactions known in the art, using reactants which are already known or which may be prepared using standard processes and techniques known in the art. In its essence, the general method for preparing the compounds of Formula I and Formula II may be depicted by the following reaction scheme I.

Unless otherwise designated, the following schemes contain variables which have the meanings previously defined. "Pg" means an appropriate protecting group. Appropriate protecting groups can be found in "*Protective groups in organic synthesis*, 2nd ed. Theodora W. Greene, John Wiley and Sons, Inc., New-York (1991), incorporated herein by reference. Some examples are THP (tetrahydropyranyl), TBDMS (tertiobutyl dimethylsilyl), TBDPS (tertiobutyl-diphenyl-silyl). Subscripts on Pg are used to differentiate the protecting groups so that some protecting groups can be selectively cleaved leaving the others intact. "B" or "BASE" means nucleic base as defined herein. "DEAD" means Diethylazodicarboxylate. "TMS Br" means trimethylsily Bromide. "Ph" means phenyl. "K$_2$CO$_3$" means potassium carbonate. "DMF" means dimethylformamide. M⊕ means pharmaceutically acceptable alkali metal cation. "n" is 1 or 2.

Schemes I through III show how to make the intermediates (3), (6) and (9) of Scheme A. Schemes IV through VI show synthesis starting from intermediates (3), (6) and (9). Scheme A shows an overview of how most of the schemes fit together. Scheme B is an alternative synthesis for a portion of Scheme A whereas Scheme C is an additional to Scheme A. Schemes D, E and F are directed to variables at the $R_3$ and $R_4$ positions.

SCHEME I:
Preparation of intermediate (3)
(When T is a saturated moiety)

$$X-CH_2-Y_1-W-(CH_2)_n-OPg_1 \quad (1)$$

$(RO)_3P, \Delta$ | Step a: Arbuzov reaction $$\underset{\|}{O}$$
$$(RO)_2P-CH_2-Y_1-W-(CH_2)_n-OPg_1 \quad (2)$$

Step b: Selective deprotection of $Pg_1$ $$\underset{\|}{O}$$
$$(RO)_2P-CH_2-Y_1-W-(CH_2)_n-OH \quad (3)$$

$W=W_a, W_b, W_c,$ or $W_d$.
$Y_1=CH_2$, $CH(OPg_2)$, $OCH_2$, $OCH(CH_2OPg_2)$, $CH(CH_2OPg_2)CH_2$, $CH(CH_2OPg_2$, or $CH_2CH(CH_2OPg_2)$.
n=1 or 2.
X=halide (Cl, Br, I).
R=$C_{1-15}$ alkyl or benzyl.

Typically the preparation of the compounds of type (3) produced by Scheme I in step a use an Arbuzov reaction by heating a trialkylphosphite or triarylphosphite moiety and a suitably protected alcohol halide of type (1) Engel R. et al., *Chem. Rev.* 77: 349 (1977) and Holy A. et al., *Collect. Czech. Chem. Commun.* 52: 2801 (1987). The hydroxy protecting groups $Pg_1$ and $Pg_2$ are selected to be stable at the reaction conditions and also to be cleaved selectively after the completion of the reaction in step b to afford compound of type (3).

SCHEME II:
Preparation of Intermediate (6)
(when T is an unsaturated moiety)

$$OHC-Y_2-W-(CH_2)_n-OPg_2 \quad (4)$$

$[(RO)_2P(O)]_2CH^{\ominus}M^{\oplus}$ or
$(RO)_2P(o)\text{-}CH=P-Ph_3$ | Step a: Wittig reaction

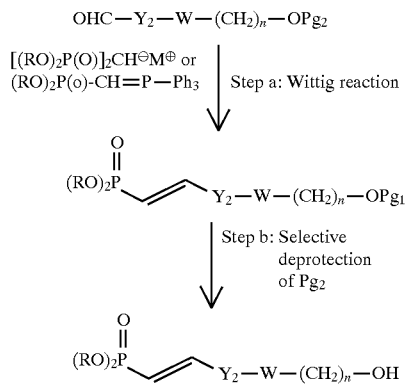

(5)

Step b: Selective deprotection of $Pg_2$ (6)

$Y_2$=nothing, $CH(OPg_2)$ or $CH_2(CH_2OPg_2)$, provided that when $Y_2$=O then W does not equal Wc. W=same as Scheme A.
R=$C_{1-15}$ alkyl or benzyl.

In Scheme II compounds of type (6) are obtained by a Wittig type reaction according to Jones G. and Moffat, *J. Org. Chem.* (1968), Waszkuc W. et al., Synthesis 1025 (1984) with aldehydes of type (4). For example the appropriate aldehyde of type (4) is reacted with a slight excess of one molar equivalent of the lithium salt of tetraethylenebisphosphonate in a aprotic solvent such as tetrahydrofuran. The reactants are typically stirred together for a time period ranging from 10 to 24 hours at a temperature range of about −78° C. The corresponding alkenyl phosphonate (5) is recovered from the reaction mixture by extractive methods well known in the art. In step b the hydroxy protecting group $Pg_1$ is selectively cleaved to afford the alcohol of type (6).

SCHEME III:
Preparation of intermediate (9)
(When the T moiety contains an Oxygen)

$$X-Y_3-W-(CH_2)_n-OPg_1 \quad (7)$$

$$\underset{\|}{O}$$
$$(RO)_2P-CH_2O^{\ominus}M^{\oplus} \quad | \quad \text{Step a}$$

$$\underset{\|}{O}$$
$$(RO)_2P-CH_2-O-Y_3-W-(CH_2)_n-OPg_1 \quad (8)$$

Step b: selective deprotection of $Pg_1$ $$\underset{\|}{O}$$
$$(RO)_2P-CH_2O-Y_3-W-(CH_2)_n-OH \quad (9)$$

$Y_3=CH_2$ or $CH(CH_2OPg_2)$.
W=same as Scheme A.
X=leaving group such as mesylate, tosylate, triflate, or halide (Cl, Br, I).
R=$C_{1-15}$ alkyl or benzyl.
alternatively $$HO-Y_3-W-(CH_2)_n-OPg_2 \quad (10)$$

$$\underset{\|}{O}$$
$$(RO)_2P-CH_2-X, \text{Base} \quad | \quad \text{Step a}$$

$$\underset{\|}{O}$$
$$(RO)_2P-CH_2-O-Y_3-W-(CH_2)_n-OPg_2 \quad (8)$$

X=Tosylate or mesylate.
W, Pg and $Y_3$=as previously defined.
R=$C_{1-15}$ alkyl or benzyl.

In Scheme III compounds of type (8) are obtained in step a by a nucleophilic displacement of an allylic, propargylic or allenic halide of type (7) by the alkoxide anion of hydroxymethylphosphonic acid diester in an aprotic solvent such as tetrahydrofuran or dimethylformamide at temperature ranging from −10° C. to 50° C. for a time period of 6 to 24 hours. In step b the hydroxy protecting group $Pg_1$ is selectively cleaved to give the alcohol of type (9).

Alternatively compounds of type (8) could be obtained by a nucleophilic displacement of the tosyloxymethylphosphonic acid diester by the alkoxide anion of the alcohol of type

(10) in the same reactions conditions described above.

SCHEME IV:
Starting with intermediates (3), (6) or (9)
from schemes I, II and III

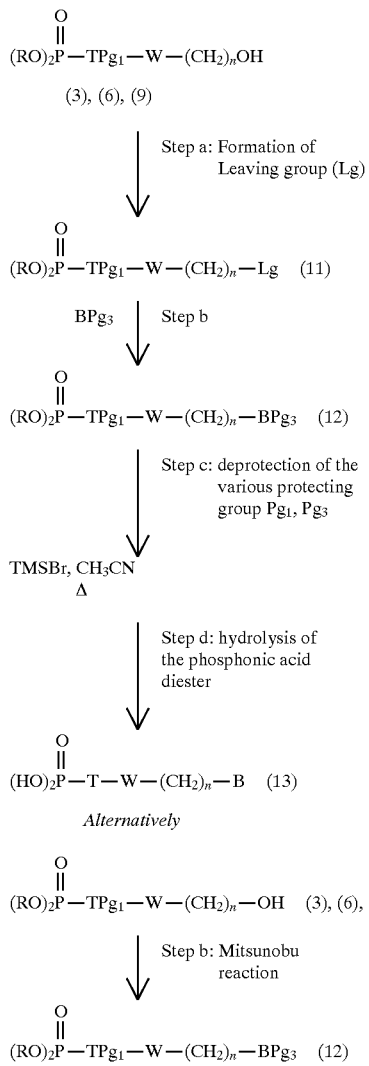

Lg=Tosylate , Mesylate , Trifate, Cl, Br, or I.
Pg, B and W=as previously defined.
R=$C_{1-15}$ alkyl or benzyl.

In Schemes IV, V, VI to the respective compounds (3), (6), or (9) are added the appropriate purine or pyrimidine base as defined herein to give independently compounds (13), (16) and (19).

In Scheme IV the replacement of the hydroxy function by a nucleic base in the compounds (3), (6), or (9) is achieved by transformation of the alcohol into a leaving group (step a) to give compound (11), and then react with one molar equivalent of the appropriate nucleic base (B) on the protective form (BPg3) if necessary in presence of a base such as potassium carbonate in an organic solvent such as anhydrous dimethylformamide (step b). The reactants are stirred from 10 to 48 hours at about 0° C. to room temperature to afford compound (12). Then the sequential deprotection of the base and the hydrolysis of the phosphonic acid diester with trimethylsilyl bromide can be done in a number of ways to give compound (13). Bronson J. et al. ,*J. Med. Chem.* 32: 1457 (1989) and Kim C. et al. , *J. Med. Chem.* 33: 1207 (1990). The de-esterification or deprotection steps can be reversed.

Alternatively the replacement of the hydroxy group in (3), (6) and (9) by a nucleic base could be done by a Mitsunobu reaction—Jenny T. *Tet. Lett.* 32: 7029 (1991) to give the intermediate (12) which is treated as described above to give compounds of type (13).

SCHEME V:
Starting with intermediates (3), (6) or
(9) when Z = $CH_2OCH_2$

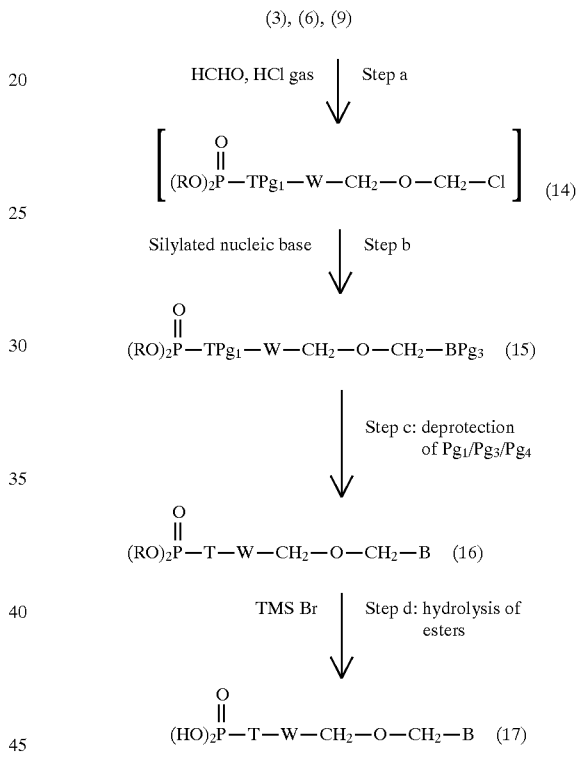

B, Pg, W and T=as previously defined.
R=$C_{1-15}$ alkyl or benzyl.

In Scheme V the formation of the methoxymethylester function (Z=$CH_2OCH_2$) linked to the nucleic base in compounds (17) is achieved by treatment of a mixture of any one of the compounds (3), (6), or (9) (when n=1) and paraformaldehyde by hydrogen chloride gas in 1,2-dichloroethane to form intermediary chloromethyl ether (14) (step a) which is treated after elimination of the excess of the acid chloride by the silylated form of the nucleic base (BTMS) obtained by treatment of the corresponding nucleic base with an excess of bis-trimethylsilylacetamide (step b). The sequential deprotection of the protecting group of the nucleic base and the hydrolysis of the phosphonic acid diester is achieved as described in Scheme I (steps c and d) to give compounds (17) Ogilvie K. et al., Can. *J. Chem.* 60: 3005 (1982) and Ogilvie K. et al.,*Nucleosides and Nucleotides* 2: 147 (1983).

SCHEME VI
Starting with intermediates (3), (6) or (9) when Z = CH$_2$—O

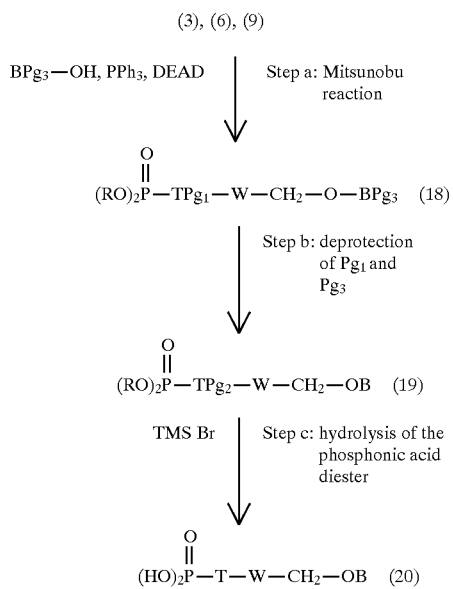

In Scheme VI the formation of compounds of type (20) containing the linkage oxygen nucleic base is achieved by a Mitsunobu type reaction coupling suitably functionalized alcohols (3), (6), or (9) with 1-hydroxypyrimidines or 9-hydroxypurine Parkin A., *J. Chem. Soc. Perkin Trans.* 2983 (1991) using triphenylphosphine, diethylazodicarboxylate in dimethylformamide (step a). The deprotection of the nucleic base and the phosphonic acid diester are achieved as described in Scheme IV.

SCHEME A

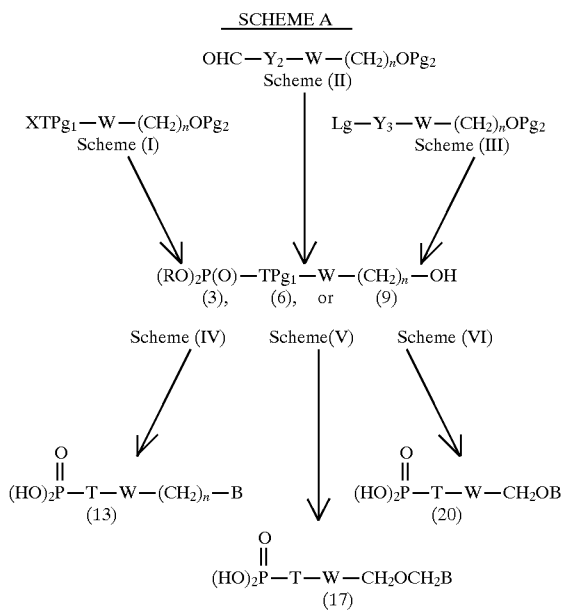

Lg=leaving group such as Tosylate, Mesylate, Trifate, Cl, Br or I.
B, W. and T=as previously defined.
X=halogeno.

R=C$_{1-15}$ alkyl or benzyl.

In the particular case of the compounds having a methylene oxymethyl attached to the phosphorus atom (T=CH$_2$OCH$_2$) a sequential alkylation of a symmetrical dihalide (chloride) could be used as follows:

SCHEME B
Alternative synthesis to Scheme A when T = CH2OCH2 and Z = CH2

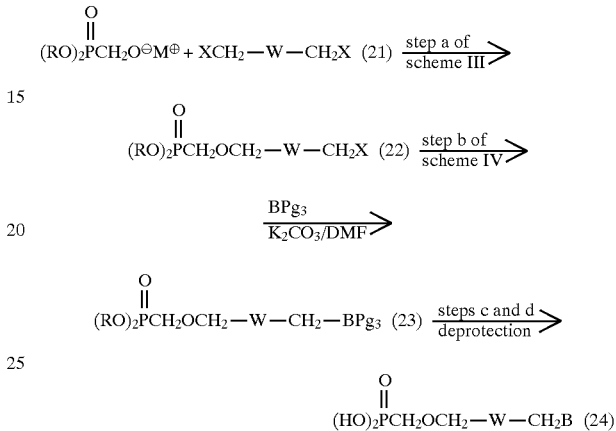

In the particular case of the introduction of a symmetrical unit of type (21) Scheme B, the substitution described in step a Scheme III and step b Scheme IV could be achieved sequentially by using the same conditions as described in the separated cases, step a of Scheme III to introduce the methoxy phosphonic acid diester to give compound (22), and step b of Scheme IV to introduce the protected nucleic base to give compound (23). The sequential deprotection of the nucleic base and the hydrolysis of the phosphonic acid diester afford compound (24).

SCHEME C
IN ADDITION TO SCHEME A, when W = CH═CH═CH.

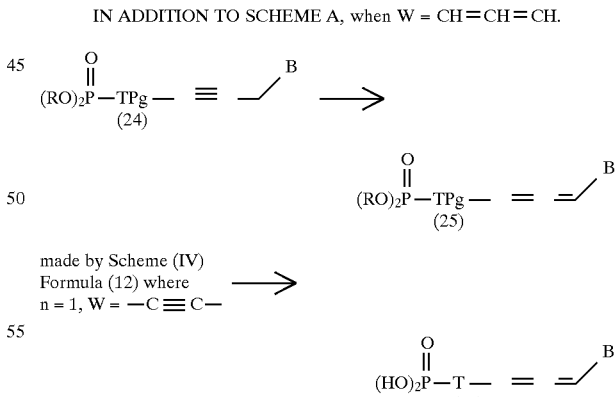

In the case of Z=zero, W is always equal to the allenyl moiety the compounds of type (26) are obtained from the ethynyl derivatives (24) (obtained by one of the methods described above depending on T) by a basic treatment to isomerize the ethynyl function into an allenyl function as it is described by Phadtar S. et al., *J. Am. Chem. Soc.* 111: 5925 (1989).

SCHEME D

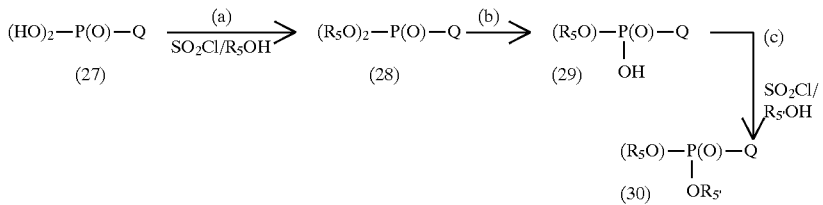

Q = T—W—Z—BASE, wherein T, W and Z are as defined in Formulas I and II and BASE represents the nucleic bases defined herein. $R_5$ and $R_{5'}$ are as previously defined.
$SO_2Cl/R_5OH$ In Scheme D, step (a), the dihydroxyphosphonate (27) is reacted with thionyl chloride to give dichlorophosphonate which is reacted further with the alcohol $R_5OH$ to give the disubstituted phosphonate (28). In step (b), the disubstituted phosphonate (28) is hydrolyzed to produce (29). In step (c), the monoacyloxyalkylmonoalkyl phosphonate (29) is reacted with thionyl chloride as previously described and further reacted with $R_5'OH$ to produce the unsymmetrically disubstituted phosphonate where $R_5$ and $R_5'$ are different.

SCHEME E

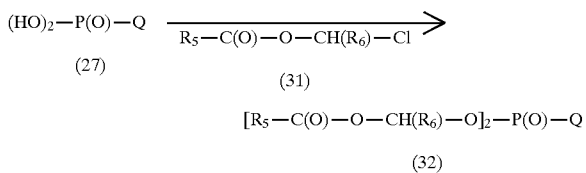

As defined in Scheme D.

Scheme E shows the dihydroxyphosphonate (27) reacting with a substituted chloromethylether (31) in the presence of an organic base such as substituted morpholine to produce the disubstituted phosphonate (32).

SCHEME F

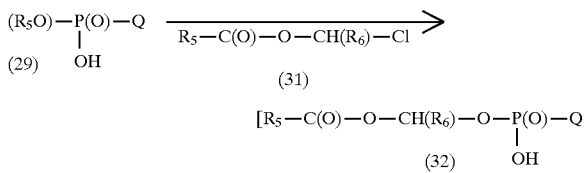

As defined in Scheme D.

Scheme F shows the monoacyloxyalkylmonoalkyl phosphonate (29) reacted with the chloromethylether (31) as previously described to produce the monoacyloxyalkyl phosphonate (32).

EXAMPLE 1

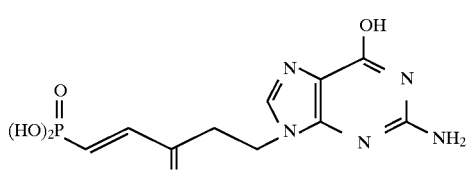

E-9-(5-Dihydroxyphosphoryl-3-methylidene-4-pentenyl) guanine (Wherein $X_1$ is $NH_2$, $X_2$ is OH, Z is $CH_2CH_2$, W is $W_a$ wherein $R_1$ and $R_2$ are each H, and T is T' which is CH=CH)

Step A:

4-t-Butyldimethyloxy-2-methylidenebutanal

A mixture of 4-t-butyldimethyloxy-2-acetyloxy-1-butanol (14 g, 50 mmol), molecular sieves in powder, N-methyl-morpholine N-oxide (9.9 g, 75 mmol) and tetrapropylammonium perruthenate (TPAP) (0.34 g, 2.5 mmol) in anhydrous dichloromethane (250 ml) is stirred overnight at 20° C. Then the reaction mixture is filtered through celite, concentrated in vacuo and the title product is purified by flash chromatography on silica gel (8.25 g, 77%).

Step B:

E-5-t-Butyldimethylsilyloxy-3-methylidene-1-pentenyl-phosphonic acid diethyl ester A solution of 1.6M of n-butyllithium in hexane (4.7 ml, 7.45 mmol) is added to a mixture of tetraethylmethylene biphosphonate (2.14 g, 7.45 mmol) in anhydrous tetrahydrofuran (70 ml) at −78° C. under argon. After 1 hour, a solution of 4-t-butyldimethyloxy-2-methylidenebutanal (1.14 g, 5.3 mmol) in anhydrous tetrahydrofuran (10 ml) is added dropwise. The reaction mixture is stirred 3 hours at −78° C., and overnight at 20° C., then hydrolyzed with a saturated solution of ammonium chloride and extracted with diethylether. The title product is isolated by flash chromatography on silica gel (1.7 g, 91%).

Step C:

E-5-Hydroxy-3-methylidene-1-pentenyl-phosphonic acid diethyl ester

A mixture of E-5-t-butyldimethylsilyloxy-3-methylidene-1-pentenyl-phosphonic acid diethyl ester (1.7 g, 4.86 mmol) and 1M tetrabutylammonium fluoride in tetrahydrofuran (8 ml, 8 mmol) is stirred 2 hours at 20° C. Then the reaction mixture is concentrated in vacuo and the title product is purified by flash chromatography on silica gel (1.1 g, 94%).

Step D:

E-5-Tosyloxy-3-methylidene-1-pentenyl-phosphonic acid diethyl ester

A mixture of E-5-hydroxy-3-methylidene-1-pentenyl-phosphonic acid diethyl ester (1.07 g, 4.6 mmol), triethylamine (0.7 ml, 5 mmol), tosylchloride (0.96 g, 5 mmol) and dimethylaminopyridine (0.005 g, 0.04 mmol) in anhydrous and dichloromethane is stirred 4 hours at 20° C., concentrated in vacuo and the title product is obtained by flash chromatography on silica gel (1.55 g, 87%).

Step E:

E-9-(5-Diethoxyphosphonyl-3-methylidene-4-pentenyl)-6-chloro-2-aminopurine

A mixture of 6-chloro-2-aminopurine (0.74 g, 4.3 mmol), sodium hydride (0.175 g, 4.3 mmol, 60% in oil) in anhydrous dimethylformamide (10 ml) is stirred 30 minutes at 20° C. Then a solution of E-5-tosyloxy-3-methylidene-1-pentenylphosphonic acid diethyl ester (1.5 g, 3.9 mmol) in anhydrous dimethylformamide (5 ml) is added and the resulting mixture is stirred overnight at 20° C. Then, the reaction mixture is concentrated in vacuo and the residue is purified by flash chromatography on silica gel to give the title product (1.1 g, 73%).

Step F:
E-9-(5-Dihydroxyphosphonyl-3-methylidene-4-pentenyl)-6-chloro-2-aminopurine A mixture of E-9-(5-diethoxyphosphonyl-3-methylidene-4-pentenyl)-6-chloro-2-aminopurine (0.96 g, 2.5 mmol) and trimethylsilylbromide (1.3 ml, 10 mmol) in anhydrous acetonitrile (5 ml) is stirred overnight at 20° C. Then the reaction mixture is treated with methanol (5 ml) and concentrated in vacuo. The crude product (0.8 g) is used in the next step without further purification.

Step G:
E-9-(5-Dihydroxyphosphonyl-3-methylidene-4-pentenyl)quanine

A mixture of crude E-9-(5-dihydroxyphosphonyl-3-methyl-idene-4-pentenyl)-6-chloro-2-aminopurine (0.8 g, ~0.245 mmol) in 1N hydrochloric acid (5 ml) is stirred overnight at 20° C. Then the reaction mixture is concentrated in vacuo, diluted with absolute ethanol to give the title product on cooling (0.46 g, 60%).

EXAMPLE 2

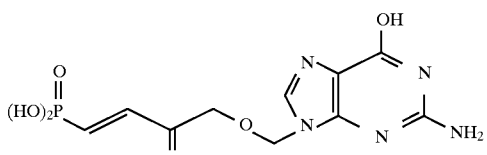

E-9-[(4-Dihydroxyphosphoryl-2-methylidene-3-butenyloxy) methyl]quanine (Wherein $X_1$ is $NH_2$, $X_2$ is OH, Z is $CH_2OCH_2$, W is $W_a$ wherein $R_1$ and $R_2$ are each H, and T is T' which is CH=CH).

Step A:
2-t-Butyldiphenylsilyloxymethyl-2-propene-1-ol

A solution of t-butyldiphenylsilylchloride (45 g, 165 mmol) in anhydrous dichloromethane (60 ml) is added dropwise to a stirred solution of 2-hydroxymethyl-2-propene-1-ol (12 g, 165 mmol) triethylamine (27.5 ml) and 4-dimethylaminopyridine (2 g) in anhydrous dichloromethane (300 ml) at 0° C. Then, the mixture is stirred at 20° C. overnight, washed with a saturated solution of ammonium chloride and brine. The title product is obtained by flash chromatography on silica gel (19.4 g, 40%).

Step B:
2-t-Butyldiphenylsilyloxymethyl-2-propenal

A mixture of 2-t-butyldiphenylsilyloxymethyl-2-propene-1-ol (25.5 g, 86.7 mmol), molecular sieves in powder (26 g), N-methylmorpholine-N-oxide (15.3 g, 130 mmol) and tetrapropylammoniumperruthenate (1.5 g, 4 mmol) in anhydrous dichloromethane (400 ml) is stirred overnight at 20° C. Then the reaction mixture is concentrated in vacuo and purified by flash chromatography on silica gel to give the title product (21 g, 83%).

Step C:
E-4-t-Butyldiphenylsilyloxy-1,3-butadienyl phosphonic diethyl ester

A solution of 1.6M of n-butyllithium in hexane (70 ml, 120 mmol) is added to a solution of tetraethylmethylene biphosphonate (34.5 g, 120 mmol) in anhydrous tetrahydrofuran (150 ml) at −78° C. After 30 minutes, a solution of 2-t-butyldiphenylsilyloxymethyl-2-propenal (21 g, 71.5 mmol) in anhydrous tetrahydrofuran is added dropwise. The reaction mixture is stirred 4 hours at −78° C. and overnight at 20° C. and then hydrolyzed with a saturated solution of ammonium chloride and extracted with diethylether. The title product is obtained by flash chromatography on silica gel (20 g, 55%).

Step D:
E-4-Hydroxy-1,3-butadienylphosphonic acid diethylester

A mixture of E-4-t-butyldiphenylsilyloxy-1,3-butadienyl phosphonic diethyl ester (11 g, 26.4 mmol) and tetrabutylammonium fluoride trihydrate (10 g, 31 mmol) in tetrahydrofuran (100 ml) is stirred 2 hours at 20° C. The reaction mixture is concentrated in vacuo, diluted with ethyl acetate and washed with brine. The title product is obtained by flash chromatography on silica gel (4.6 g, 80%).

Step E:
E-9-[(4-Diethoxyphosphoryl-2-methylidene-3-butenyloxy)-methyl]-6-(2-trimethylsilylethyloxy)-2-aminopurine Anhydrous hydrochloric acid is bubbled into a mixture of paraformaldehyde (0.17 g, 5.0 mmol) E-4-hydroxy-1,3-butadienylphosphonic acid diethylester (0.9 g, 4.5 mmol) in anhydrous 1,2-dichloroethane (5 ml) at 0° C. for 15 minutes. The reaction mixture is stirred 2 hours at 20° C., concentrated in vacuo and diluted with 1,2-dichloromethane (10 ml) and added to a solution of bistrimethylsilyl-6-(2-trimethylsilylethyloxy)-2-aminopurine obtained by heating at 60° C., 6-(2-trimethylsilylethyloxy)-2-aminopurine (1.3 g, 5 mmol) and bistrimethylsilylacetamide (2.5 g) in 1,2-dichloroethane (5 ml) during 1 hour and tetrabutylammonium iodide (0.19 g, 0.5 mmol). The reaction mixture is stirred 3 hours at 20° C., then 4 hours under reflux and hydrolyzed with a saturated solution of ammonium chloride and extracted with chloroform. The title product is obtained by flash chromatography on silica gel (0.37 g, 96%).

Step F:
E-9-[(4-Dihydroxyphosphonyl-2-methylidene-3-butenyloxy)-methyl]quanine

A mixture of E-9-[(4-diethoxyphosphonyl-2-methylidene-3-butenyloxy) methyl]-6-(2-trimethylsilylethyloxy)-2-amino-purine (0.24 g, 0.5 mmol) and trimethylsilylbromide (0.26 ml, 2 mmol) in anhydrous acetonitrile (3 ml) is stirred overnight at 20° C. The reaction mixture is treated with methanol (2 ml), concentrated in vacuo and the title product is obtained by crystallization in ethanol: water (0.12 g, 65%).

EXAMPLE 3

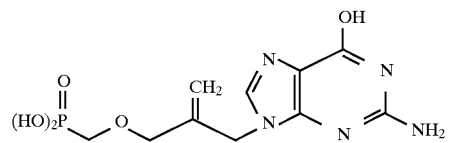

9-(3-Dihydroxyphosphorylmethoxy-2-methylidene propyl)quanine (Wherein $X_1$ is $NH_2$, $X_2$ is OH, Z is $CH_2$, W is $W_a$ wherein $R_1$ and $R_2$ are each H, and T is T''' which is $CH_2OCH_2$)

Step A:
(2-Chloromethyl-2-propenyloxymethyl)phosphonic acid diethylester

To a mixture of hydroxymethylphosphonic acid diethylester (0.84 g, 5 mmol), 1-chloro-2-chloromethyl-2-propene (0.95 g, 7.6 mmol) and tetrabutylammonium iodine (0.18 g, 0.5 mmol) in anhydrous tetrahydrofuran (10 ml), sodium hydride is added (0.24 g, 6 mmol 60% in oil) at 0° C. The mixture is stirred overnight at 20° C. The reaction mixture is hydrolyzed with a saturated solution of ammonium chloride, extracted with ethyl acetate and the title product is obtained by flash chromatography on silica gel (0.35 g, 27%).
Step B:
9-(3-Diethoxyphosphorylmethoxy-2-methylidene propyl) 6-chloro-2-aminopurine A mixture of (2-chloromethyl-2-propenyloxymethyl)-phosphonic acid diethylester (0.285 g, 1.1 mmol), 6-chloro-2-aminopurine (0.25 g, 1.5 mmol) and potassium carbonate (0.24 g, 1.5 mmol) in anhydrous dimethylformamide is stirred 2 days at 20° C. Then the reaction mixture is concentrated in vacuo and the title product is obtained by flash chromatography on silica gel (0.22 g, 51%).
Step C:
9-(3-Dihydroxyphosphonylmethoxy-2-methylidene propyl)-guanine A mixture of 9-(3-diethoxyphosphorylmethoxy-2-methylidene propyl)6-chloro-2-aminopurine (0.22 g, 0.56 mmol), trimethylsilylbromide (0.43 g, 2.8 mmol) and 2,6-lutidine (0.59 g, 5.5 mmol) in anhydrous acetonitrile (2 ml) is stirred 24 hours at 20° C. under argon. Then, the reaction mixture is concentrated in vacuo and treated with 1M sodium hydoxyde (10 ml) 2 days at 20° C. The title product is obtained by precipitation with ethanol (0.11 g, 61%).

EXAMPLE 4

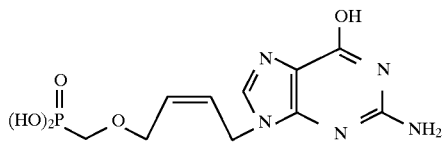

Z-9(4-Dihydroxyphosphorylmethoxy-2-butenyl)quanine (Wherein $X_1$ is $NH_2$, $X_2$ is OH, Z is $CH_2$, W is $W_c$ wherein each of $R_1$ and $R_2$ are H, and T is T'' which is $CH_2OCH_2$)
Step A:
Z-(4-Chloro-2-butenyloxy)methyl phosphonic acid diethylester To a mixture of hydroxymethyl phosphonic acid diethylester (1.68 g, 10 mmol), Z-1,4-dichloro-2-butene (1.9 g, 15 mmol) and tetra-n-butylammonium iodide (0.36 g, 1 mmol) in anhydrous tetrahydrofuran (15 ml), sodium hydride (0.48 g, 12 mmol, 60% in oil) is added at 0° C. The resulting mixture is stirred overnight at 20° C., hydrolyzed with a saturated solution of ammonium chloride and extracted with diethylether. The title product is obtained by flash chromatography on silica gel (1.2 g, 45%).
Step B:
Z-9-(4-Diethoxyphosphorylmethoxy-2-butenyl)6-chloro-2-aminopurine A mixture of Z-(4-chloro-2-butenyloxy)methyl phosphonic acid diethylester (1.05 g, 4 mmol), 6-chloro-2-aminopurine (1 g, 6 mmol) and potassium carbonate (0.92 g, 6 mmol) in anhydrous dimethylformamide (10 ml) is stirred 2 days at 20° C. The reaction mixture is concentrated in vacuo and the residue is purified by flash chromatography on silica gel to give the title product (0.85 g, 55%).
Step C:
Z-9(4-Dihydroxyphosphorylmethoxy-2-butenyl)quanine A mixture of Z-9-(4-Diethoxyphosphonylmethoxy-2-butenyl) 6-chloro-2-aminopurine (0.78 g, 2 mmol), trimethylsilyl bromide (1.5 g, 10 mmol) and 2,6-lutidine (2.15 g, 20 mmol) in anhydrous acetonitrile (10 ml) is stirred 24 hours at 20° C. under argon. The reaction mixture is concentrated in vacuo, and the residue is treated with 1M sodium hydroxide (15 ml) 2 days at 20° C. The sodium salt of the title product is obtained by successive precipitation in ethanol: water (0.55 g, 75%).

EXAMPLE 5

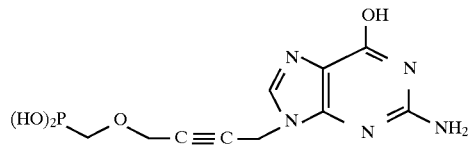

9-(4-Dihydroxyphosphorylmethoxy-2-butynyl)guanine (Wherein $X_1$ is $NH_2$, $X_2$ is OH, Z is $CH_2$, W is $W_d$, and T is T''' which is $CH_2OCH_2$).
Step A:
(4-Chloro-2-butynyloxy)methylphosphonic acid diethylester To a mixture of hydroxymethylphosphonic acid diethylester (3.35 g, 20 mmol), 1,4-dichloro-2-butyne (3.8 g, 30 mmol) and tetra-n-butylammonium iodide,(0.75 g, 2 mmol) in anhydrous tetrahydrofuran (100 ml), sodium hydride (0.95 g, 24 mmol, 60% in oil) is added in portions at 0° C. The resulting mixture is stirred overnight at 0° C. Then the reaction mixture is stirred overnight at 20° C., hydrolyzed with a saturated solution of ammonium chloride and extracted with diethylether. The title product is obtained by flash chromatography on silica gel (2.3 g, 30%).
Step B:
9-(4-Diethoxyphosphorylmethoxy-2-butynyl)-6-chloro-2-aminopurine A mixture of (4-chloro-2-butynyloxy)methylphosphonic acid diethylester (2.03 g, 8 mmol), 6-chloro-2-aminopurine (2 g, 12 mmol) and potassium carbonate (1.85 g, 12 mmol) in anhydrous dimethylformamide (15 ml) is stirred 2 days at 20° C. under argon. The reaction mixture is concentrated in vacuo, and the residue is purified by flash chromatography on silica gel to give the title product (1.7 g, 65%).
Step C:
9-(4-Dihydroxyphosphorylmethoxy-2-butynyl)guanine A mixture of 9-(4-diethoxyphosphorylmethoxy-2-butynyl)-6-chloro-2-aminopurine (1.5 g, 4 mmol), trimethylsilyl-bromide (3 g, 20 mmol) and 2,6-lutidine (4.3 g, 40 mmol) in anhydrous acetonitrile (20 ml) is stirred 1 day at 20° C. under argon. The reaction mixture is concentrated in vacuo, and the residue is treated with 1M sodium hydroxide (20 ml) 2 days at 20° C. The sodium salt of the title product is obtained by successive precipitation in ethanol: water (1.05 g, 70%).

EXAMPLE 6

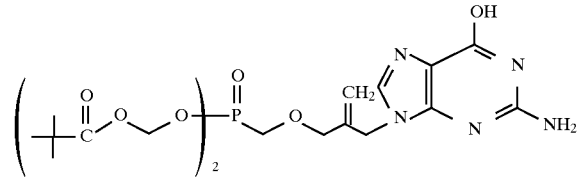

9-(3-Dipivaloylmethoxyphosphonylmethoxy-2-methylidenepropyl) guanine (Wherein $X_1$ is $NH_2$, $X_2$ is OH, Z is $CH_2$, W is $W_a$ wherein $R_1$ and $R_2$ are each H, and T is T''' which is $CH_2OCH_2$, and $R_3$ and $R_4$ are each —O—CH($R_6$)—O—C(O)$R_5$ wherein $R_6$ is H.)

N, N'-dicyclohexylcarbodiimide (1.13 g, 0.4 mmol) and chloromethylpivalate (1.8 g 12 mmol) are added to a mixture of 9-(3-Dihydroxyphosphorylmethoxy-2-methylidenepropyl) guanine (630 mg, 2 mmol) in anhydrous DMF(10 ml). The mixture is stirred at 20° C. overnight, then the insolubles are filtered off and the fluid concentrated in vacuo. The residue is diluted with toluene and washed with water. The title compound is purified by flash chromatography on silica gel eluting with 5% MeOH/$CH_2$.

EXAMPLE 7

Nucleic base modification
Adenine derivatives

In all the experiments where 6-chloro-2-aminopurine was used, adenine could be used to give the corresponding 9-substituted adenine followed by deprotection of the phosphonic diester by trimethylsilylbromide treatment.

Cytosine derivatives

In all experiments, 4-N-Acetylcytosine could be used instead of 6-Chloro-2-aminopurine. The deprotection can be carried out in 2 steps:

a) treatment with ethanolic ammonia to remove the N-Acetyl group, and b) treatment by trimethylsilylbromide to hydrolyze the phosphonate acid diester.

Thymine derivatives

In all experiments thymine can be used instead of 6-Chloro-2-aminopurine. Hydrolysis of the phosphonic acid diester can be accomplished by treatment with trimethylsilylbromide.

2,6-Diaminopurine

The diaminopurine analogs can be obtained by trimethylsilylbromide treatment or by using 2,6-diaminopurine instead of 6-chloro-2-aminopurine in the corresponding experiments.

The compounds of this invention are useful in the medical therapy particularly for the treatment or prophylaxis of viral infections such as for example antiviral agents effective against DNA viruses (herpes viruses 1 and 2, cytomegalovirus, varicella-zoster virus, Epstein-Barr virus), retroviruses (human immunodeficiency viruses 1 and 2 and visna virus) and related clinical conditions such as AIDS-related complex (ARC) and against viruses involved in tumor formation. The antiviral agents of the present invention have usefulness as monotherapy agents and in conjunction with other antiviral agents such as in conjunctive therapy for the treatment of retroviral infections, especially in humans, particularly human immunodeficiency virus. Particularly preferred is conjunctive therapy with 2',3'-dideoxy purine nucleosides are 2'3'-dideoxyadenosine, 2',3'-dideoxyguanosine, 2',3'-dideoxythioinosine and 2',3'-dideoxyinosine. Other possible conjunctive therapy include agents that are effective for the treatment or prophylaxis of viral infections or associated conditions such as 3'-azido-3'-deoxythymidine (zidovudine), 2',3'-dideoxynucleosides such as 2',3'-dideoxycytidine, 2',3'-dideoxy adenosine and 2',3'-dideoxyinosine, acyclic nucleosides (e.g. acyclovir), interferons such as α-interferon, renal excretion inhibitors such as probenicid, nucleoside transport inhibitors such as dipyridamole, as well as immuno-modulators such as inter-leukin II and granulocyte macrophage colony stimulating factors. The component compounds of such combination therapy may be administered simultaneously, in either separate or combined formulations, or at different times, e.g., sequentially such that a combined effect is achieved.

The antiviral efficacy of the compounds of the present invention may be determined by any appropriate method. Some representative methods of testing the efficacy of these compounds follow.

MTT cell viability assay for Human Immunodeficiency virus (HIV)

The MTT cell viability assay was originally described by Pauwels et al., (J. Virol. Methods, 1988: 20, 309–321). It is a calorimetric assay based on the ability of viable but not dead cells to reduce yellow colored 3-(4,5-dimethyl-2-yl)-2,5-diphenyl-tetrazolium bromide (MTT) (Sigma Chemical Co. Ltd.) to a blue formazan product. This reduction reaction is carried out by mitochondrial dehydrogenases of metabolically active cells. The assay permits a rapid and accurate estimate of the anti-HIV activity of potential antiviral agents in parallel with their cytotoxicity enabling selectivity indices (S.I) to be determined.

MT-4 cells which are highly susceptible to HIV infection are used infected with the HIV-1 strain RF. The central 60 wells of plastic 96 well flat-bottomed microtitre trays (Sterilin Ltd.) are filled with 100 μl of growth medium containing serial dilutions of the test compounds at twice the required final concentration. The outside wells are filled with sterile distilled water to prevent evaporation during the incubation period. For each concentration of compound, there are two sets of triplicate wells, so that the effect of the compound on both infected and uninfected cells can be evaluated simultaneously. Some wells are left drug free as untreated controls for both mock- and virus-infected cells. Exponentially growing MT-4 cells are counted and the number of cells adjusted to allow $5 \times 10^4$ cells per well. The cells are then pelleted and divided into two. Half of the cells are infected with virus (100TCID50 per $5 \times 10^4$ cells) and the other half mock infected. Virus adsorption is for one hour at room temperature. The cells are then pelleted and washed once in RPMI prior to being resuspended in a volume of medium such that 100 μl can be added to each well of the microtitre plate. The culture plates are incubated at 37° C. in an incubator containing 5% with $CO_2$.

After six days incubation, 10 μl of a solution of MTT (7.5 mg/ml) in PBS is added to each well and the plates incubated for a further one hour at 37° C. The formazan crystals are solubilized by adding 100 μl of 10% (v/v) Triton X-100 in acidified isopropanol (2 ml concentrated HCl per 500 ml solvent) and mixing. Finally the absorbance is read at 540 nm using a Multiskan MCC spectrophotometer (Flow Laboratories). For each compound, the mean optical density (O.D.) readings for both mock- and virus-infected cells are plotted against the drug concentration. The O.D. value representing the 50% endpoint from which both the 50% cytotoxic dose (CD50) and 50% inhibitory concentration (IC50) of the test compounds can be determined is calculated using the following formula:

mean O.D. mock infected—mean O.D. virus infected/2

Protocol for Detection of Anti-HIV Activity of Compounds Using C-8166

The central 60 wells of plastic 96 well flat-bottomed microtitre trays are filled with 100 μl of growth medium containing serial dilutions of the test compounds at twice the required final concentration. The outside wells are fitted with sterile distilled water to prevent evaporation during the incubation period. Triplicate wells are used for each concentration of compound. Some wells are left drug free as untreated controls. Exponentially growing C-8166 cells are counted and the number of cells adjusted to allow $1\times10^5$ cells per well. The cells are pelleted and infected with HIV to give a multiplicity of infection of between 0.001 and 0.0001 infectious units per cell.

Virus adsorption is for one hour at room temperature. The cells are then pelleted and washed three times in RPMI prior to being resuspended in a volume of medium such that 100 $\mu$l can be added to each well of the microtitre plates. The culture plates are incubated at 37° C. in an incubator containing 5% $CO_2$. After three days the infected cells are observed and scored for the presence of syncytia: +++= 50%–100% cpe; ++=10%–50% cpe;+=<10% cpe and O=no syncytia. 100 $\mu$l of supernatant fluid is then harvested from each well and assayed for levels of p24 viral core antigen using an ELISA.

p24 ELISA

The central 60 wells of 96 well 'U' bottomed microtitre plates (Falcon, Becton Dickinson) are coated with 100 $\mu$l of an affinity purified sheep anti-HIV-1-p24 (Aalto Bioreagents, Rathfarnham, Dublin, Ireland, code D7320) at a concentration of 10 $\mu$g/ml in coating buffer (100 mM $NaHCO_3$ pH 8.5). This product was produced by immunizing sheep with three different synthetic peptides corresponding to amino acids 283–297 (LDIRQGPKEPFRDYV); 173–188 (SALSEGATPQDLNTML) AND 226–237 (GQMREPRGSDIA) of the p24 gag protein of HIV-1 strain BH-10. The plates are left for the antibodies to attach, at +4° C. overnight and then washed twice in Tris buffered saline (TBS) (0.144M NaCl, 25 mM Tris pH 7.5) using a microtitre plate washer (Luminar Technologies) prior to being blocked with 2% skimmed milk (Cadburys Marvel) made up in TBS for 1 hour at room temperature (200 $\mu$l/well). After two washes with TBS, 100 $\mu$l volumes of cell free culture fluid are added to the wells along with 10 $\mu$l of a 1% (v/v) solution of the zwitterionic detergent Empigen (Calbiochem). Depending on the expected levels of p24, the culture fluids are screened either neat or at 1:10 or 1:100 dilutions. The samples are incubated at room temperature overnight prior to the wells being washed three times and incubated with 100 $\mu$l of a second anti-p24 anti-body, EH12E1-AP directly conjugated to alkaline phosphatase (ADP 452) at a concentration of 1:3000 in TBS containing 20% sheep sera (Seralab), 2% skimmed milk (Cadburys Marvel) and 0.5% Tween 20 (Sigma Chemical Co.). This antibody raised against the HIV-1 CB1-1 isolate by Bridget Ferns, Richard Tedder and colleagues at the Middlessex Hospital Medical School has been mapped to a complex epitope incorporating two distinct peptide sequences. These are GHQAAMQM-LKETINEEAAEWDRVHPVHAGPIAPGQ (aa 193–227) and NPPIPVGEIYKRWII (aa 253–267) and are conserved between HIV-1 strains. The alkaline phosphatase conjugate of EH12E1 (EH12E1-AP) was prepared by Novo BioLabs, Cambridge, U.K. This conjugated antibody was obtained through the ADP reagent bank. The plates are incubated at 37° C. for 1 hour using an incubator/shaker (Luminar Technologies) and then the wells washed three times in TBS. The wells are given a final wash in buffer provided in the commercially available alkaline phosphatase detection and amplification kits, AMPAK (IQ (Bio) Ltd.) and 50 $\mu$l of the AMPAK substrate added according to the manufacturers instructions. After 30 minutes at room temperature, 50 $\mu$l of the AMPAK amplifier is added and the purple color intensity read after stopping the reaction with acid at 492 nm using a Multiskan MCC/340 Spectrophotometer (Flow Laboratories) after approximately ten minutes.

The immunoassay is calibrated using recombinant HIV-1p24 (American Biotechnologies Inc.) obtained through the ADP, using a series of doubling dilutions starting at 100 ng/ml. This assay usually gives a linear response over the range 300 to 10,000 pg/ml, although there is day to day variation.

Detection of the Anti-Herpes (HSV-1 and HSV-2 Activity of Compounds

For assay, HeLa (human cervical carcinoma) cells (0.8× $10^5$/0.1 ml) or Vero (African Green Monkey kidney) cells (1.0×$10^5$/0.1 ml) in the appropriate growth medium were transferred to flat-bottomed, 96 well (0.1 ml cells/well) microtitre plates (Falcon). After 24 hours' incubation at 37° C. in a humidified $CO_2$ (5% $CO_2$, 95% air) incubator the cultures were ready for use.

For each assay the growth medium was aspirated from the microtitre plate cultures and replaced with 100 $\mu$l maintenance medium (cell and virus controls) or compound diluted to twice test concentration in maintenance medium (toxicity controls, test wells). After 3 hours' incubation at 37° C. in a humidified $CO_2$ incubator each culture received 100 $\mu$l maintenance medium (cell and toxicity controls) or virus [Herpes simplex virus type 1 (HSV-1; strain HF, ATCC VR-260) or Herpes simplex virus type 2 (HSV-2; strain G, ATCC VR-734)] diluted in maintenance medium (virus controls, compound test wells). All cultures were then incubated at 37° C. and examined microscopically at 48 and 72 hours (Herpes) or 7, 10 and 14 days (CMV) for virus- and compound-induced cytopathic effect (CPE). CPE was graded as 0 (no), 1+ (25%), 3+ (75%) or 4+ (100%) cell monolayer destruction. These data were then used to calculate the 50% compound inhibitory concentrations ($IC_{50}$'s).

Detection of the Anti-cytomegalovirus Activity of Compounds

For assay, MRC-5 cells (1.2×$10^5$/0.1 ml) in the appropriate growth medium were transferred to flat-bottomed, 96 well (0.1 ml cells/well) microtitre plates (Falcon). After 24 hours' incubation at 37° C. in a humidified $CO_2$ (5% $CO_2$, 95% air) incubator the cultures were ready for use.

For each assay the growth medium was aspirated from the microtitre plate cultures and replaced with 100 $\mu$l maintenance medium (cell and virus controls) or compound diluted to twice test concentration in maintenance medium (toxicity controls, test wells). After 3 hours' incubation at 37° C. in a humidified $CO_2$ incubator each culture received 100 $\mu$l maintenance medium (cell and toxicity controls) or virus [Human Cytomegalovirus (CMV, strain AD-169, ATCC VR-538)] diluted in maintenance medium (virus controls, compound test wells). All cultures were then incubated at 37° C. and examined microscopically at 48 and 72 hours (Herpes) or 7, 10 and 14 days (CMV) for virus- and compound-induced cytopathic effect (CPE). CPE was graded as 0 (no), 1+(25%), 3+(75%) or 4+(100%) cell monolayer destruction. These data were then used to calculate the 50% compound inhibitory concentrations ($IC_{50}$'s).

The efficiency of phosphorylation (defined as the Vmax/ Km ratio) of the acyclonucleotide derivatives of guanine by guanylate kinase was compared to that of GMP, used as reference substrate. The assay used for determination of the parameters Vmax and Km was as described by Nave et al. in Arch. Biochem. Biophys. (1992), 295, 253–257.

The amount of the active ingredient to be administered can vary widely according to the particular dosage unit employed, the period of treatment, the age and sex of the patient treated and the nature and extent of the disorder treated. The total amount effective antiviral amount of the active ingredient to be administered will generally range from about 1 mg/kg to 100 mg/kg and preferably from 3 mg/kg to 25 mg/kg. A unit dosage may contain from 25 to 500 mg of active ingredient, and can be taken one or more times per day. The active compound of formula I or II can be administered with a pharmaceutical carrier using conventional dosage unit forms either orally, parenterally, topically or transdermally.

As used herein the term "patient" includes mammals such as mice, rats, cats, dogs, cattle, sheep, swine, and primates including humans.

For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethyl-enepolypropylene copolymers; and amphoteric detergents, for example, alkyl-beta-aminopropionates, and 2-alkylimidazbline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety. Topical administration also includes incorporation of compounds of the present invention into solutions or suspensions suitable for administration to eyes or ears.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The following chart represents some of the preferred compounds of the present invention in which each of $R_1$ and $R_2$ when present represent hydrogen and each $R_3$ and $R_4$ represents OH.

| $X_1$ and $X_2$ | $X_3$ and $X_4$ | Z | W | T |
|---|---|---|---|---|
| $NH_2$, OH | | $CH_2$ | $W_a$ | CH=CH |
| $NH_2$, OH | | $CH_2OCH_2$ | $W_a$ | CH=CH |
| $NH_2$, OH | | $CH_2$ | $W_a$ | $CH_2OCH_2$ |
| $NH_2$, OH | | $CH_2$ | $W_c$ | $CH_2OCH_2$ |
| $NH_2$, OH | | $CH_2$ | $W_d$ | $CH_2OCH_2$ |
| $NH_2$, $NH_2$ | | $CH_2$ | $W_a$ | $CH_2OCH_2$ |
| $NH_2$, $NH_2$ | | $CH_2$ | $W_c$ | $CH_2OCH_2$ |
| | H, $NH_2$ | $CH_2$ | $W_a$ | $CH_2OCH_2$ |
| | H, $NH_2$ | $CH_2$ | $W_c$ | $CH_2OCH_2$ |
| | H, $NH_2$ | $CH_2$ | $W_d$ | $CH_2OCH_2$ |
| $NH_2$, $NH_2$ | | $CH_2$ | $W_d$ | $CH_2OCH_2$ |
| H, $NH_2$ | | $CH_2$ | $W_d$ | $CH_2OCH_2$ |
| H, $NH_2$ | | $CH_2$ | $W_a$ | $CH_2OCH_2$ |
| H, $NH_2$ | | $CH_2$ | $W_b$ | $CH_2OCH_2$ |
| H, $NH_2$ | | $CH_2$ | $W_c$ | $CH_2OCH_2$ |

The following chart represents preferred compounds of the present invention where $X_1$ and $X_2$ are respectively $NH_2$ and OH, Z is $CH_2$, W is $W_a$ and T is $CH_2OCH_2$. $R_5$ and $R_5'$ are each $CH_3$, $CH_2CH_3$, $CH(CH_3)_2$, $CH_2C(CH_3)_3$ or benzyl, but $R_5$ and $R_5'$ are not the same.

| $R_3$ | $R_4$ |
|---|---|
| OH | $OR_5$ |
| $OR_5$ | $OR_5'$ |
| $OR_5$ | $OR_5$ |
| $OR_5$ | $OCH_2OC(O)R_5$* |
| $OCH_2OC(O)R_5$* | $OCH_2OC(O)R_5'$* | also includes tert-butyl as $R_5$ or $R_5'$.

What is claimed is:

1. A compound of the formula:

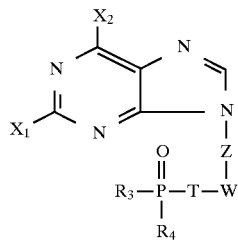

the stereoisomeric forms and mixtures thereof, tautomeric forms or the pharmaceutically acceptable salts thereof, wherein $X_1$ is H or $NH_2$;
$X_2$ is OH or $NH_2$;
Z is nothing, $CH_2$, $CH_2CH_2$, or $CH_2O$;
W is

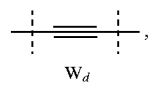

wherein

T is nothing, T' or T'", wherein
T' is $CH_2CH_2$, and
T" is $CH_2OCH_2$, $CH_2OCH(CH_2OH)$;
$R_3$ and $R_4$ are each independently OH, $OR_5$, $OR_5'$, or —O—CH($R_6$)—O—C(O)$R_5$, provided that when one of $R_3$ and $R_4$ is OH the other is not —O—CH($R_6$)—O—C(O)$R_5$, wherein $R_5$ and $R_5'$ are each independently $C_{1-15}$ alkyl or benzyl, and $R_6$ is H or $C_{1-10}$ alkyl.

2. The compound according to claim 1 wherein when W=$W_d$ and T=T" then Z is $CH_2$.

3. The compound according to claim 1 wherein T is T" and T" is $CH_2OCH_2$.

4. The compound according to claim 1 wherein Z is $CH_2$ or $CH_2O$.

5. The compound according to claim 1 wherein the compound is 9-(4-dihydroxyphosphorylmethoxy-2-butynyl) guanine.

6. The compound according to claim 1 wherein $X_1$ is $NH_2$ and $X_2$ is OH.

7. A pharmaceutical composition comprising a compound of claim 1 in combination with a pharmaceutically acceptable carrier.

8. A method of treating a patient for a viral infection of DNA viruses, retroviruses or viruses involved in tumor formation by administration to a patient of a sufficient amount of the compound according to claim.

9. A method of preparing a compound of the formula:

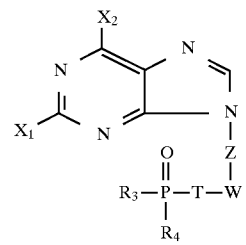

the stereoisomeric forms and mixtures thereof, tautomeric forms or the pharmaceutically acceptable salts thereof, wherein $X_1$ is H or $NH_2$;
$X_2$ is OH or $NH_2$;
Z is nothing, $CH_2$, $CH_2CH_2$, or $CH_2O$;
W is

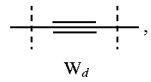

wherein

T is nothing, T' or T"', wherein
T' is $CH_2CH_2$, and
T" is $CH_2OCH_2$, $CH_2OCH(CH_2OH)$
$R_3$ and $R_4$ are each independently OH, $OR_5$, $OR_5'$, or —O—CH($R_6$)—O—C(O)$R_5$, provided that when one of R3 or R4 is OH the other is not —O—CH($R_6$)—O—C(O)$R_5$, wherein $R_5$ and $R_5'$ are each independently $C_{1-15}$ alkyl or benzyl, and $R_6$ is H or $C_{1-10}$ alkyl comprising the steps of deprotecting a compound of the formula:

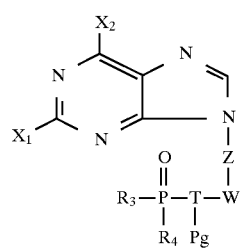
wherein $R_3$ and $R_4$ are $OR_5$, $OR_5'$ or —O—CH—($R_6$)—O—C(O)$R_5$ as previously defined and Pg is a protecting group,
and is optionally hydrolyzed to provide the compound wherein $R_3$ and $R_4$ are each —OH.
* * * * *